(12) United States Patent
Stigall et al.

(10) Patent No.: US 9,149,600 B2
(45) Date of Patent: Oct. 6, 2015

(54) DISTAL CATHETER TIP FORMATION

(71) Applicant: Volcano Corporation, San Diego, CA (US)

(72) Inventors: Jeremy Stigall, Carlsbad, CA (US); Chris LeBlanc, San Diego, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 14/134,961

(22) Filed: Dec. 19, 2013

(65) Prior Publication Data

US 2014/0180254 A1 Jun. 26, 2014

Related U.S. Application Data

(60) Provisional application No. 61/740,403, filed on Dec. 20, 2012.

(51) Int. Cl.
*A61M 25/00* (2006.01)
*B29C 63/42* (2006.01)
*B29C 65/68* (2006.01)
*B29C 65/00* (2006.01)
*B29L 31/00* (2006.01)

(52) U.S. Cl.
CPC ............. *A61M 25/001* (2013.01); *B29C 63/42* (2013.01); *B29C 65/68* (2013.01); *B29C 66/1122* (2013.01); *B29C 66/5221* (2013.01); *B29C 66/63* (2013.01); *B29C 66/71* (2013.01); *B29C 66/73152* (2013.01); *B29K 2995/007* (2013.01); *B29L 2031/7542* (2013.01)

(58) Field of Classification Search
CPC ....... B29C 63/42; B29C 65/68; A61M 25/001
USPC ................................................ 156/84, 85, 86
See application file for complete search history.

(56) References Cited

U.S. PATENT DOCUMENTS

| | | | |
|---|---|---|---|
| 4,636,272 A | | 1/1987 | Riggs |
| 4,863,442 A | * | 9/1989 | DeMello et al. .............. 604/527 |
| 6,187,130 B1 | | 2/2001 | Berard et al. |
| 7,261,850 B2 | | 8/2007 | Van Ockenburg et al. |
| 7,862,541 B2 | | 1/2011 | Jeffrey et al. |
| 2001/0016702 A1 | | 8/2001 | Benjamin |
| 2003/0135231 A1 | * | 7/2003 | Goodin et al. ................ 606/192 |
| 2011/0295234 A1 | * | 12/2011 | Eaton ............................ 604/528 |

OTHER PUBLICATIONS

International Search Report and Written Opinion received in corresponding Patent Cooperation Treaty Application No. PCT/US2013/076184 dated Apr. 21, 2014, 13 pages.

* cited by examiner

*Primary Examiner* — Philip Tucker
*Assistant Examiner* — John Blades
(74) *Attorney, Agent, or Firm* — Haynes and Boone, LLP

(57) ABSTRACT

The present disclosure provides various embodiments of methods of forming a tapering distal tip for a catheter. An exemplary method includes providing a mandrel and a holding hypotube, placing a tip first material with a first outer diameter over the mandrel and the hypotube, placing a tip second material with a second outer diameter over the mandrel and under the first material, placing a shrink tube of heat-shrink material around at least a junction of the first material and second material, heating the shrink tube, cooling the first material and second material, and removing the shrink tube and the hypotube. The first outer diameter is greater than the second outer diameter.

19 Claims, 4 Drawing Sheets

DISTAL CATHETER TIP FORMATION

CROSS-REFERENCE TO RELATED APPLICATION

The present application claims the benefit of the filing date of provisional U.S. Patent Application No. 61/740,403 filed Dec. 20, 2012. The entire disclosure of this provisional application is incorporated herein by this reference.

TECHNICAL FIELD

The present disclosure relates generally to catheters for navigating through the human vasculature, and in particular, to improved methods of forming a distal tip for a catheter.

BACKGROUND

Catheters such as intravascular catheters are well known for use in diagnostic and therapeutic applications wherein it is necessary to administer a fluid to, or otherwise contact, a precise location within the cardiovascular system, for example, by guiding the tip or distal end of the catheter through branching blood vessels. Such guiding is accomplished in part by manipulation of a proximal portion of the catheter in order to impart forces needed to curve and guide the catheter through the curving and branching blood vessels.

Generally, distal tips of catheters are made by hand. For example, an operator bonds or necks heated material over a mandrel, cools the material, and trims the material to the desired length. If the material is necked incorrectly, the operator has to reheat the part until the correct shape is achieved. The process takes both time and skill.

In addition, consistency of necking between two different operators is difficult to achieve. One operator may neck harder or heat longer than the other. Moreover, the heat being applied may not be transferred consistently between the part and heat torch so that one portion of the part will endure more or less heat.

Therefore, a need exists for methods of making distal tips for catheters that reduce human error and cost, and increase reproducibility.

SUMMARY

The present disclosure provides various embodiments of methods of forming a tapering distal tip for a catheter. In an exemplary embodiment, the method includes providing a mandrel and a holding hypotube. A tip first material, tip second material, and the holding hypotube are assembled over the mandrel. Specifically, the first material is placed over the mandrel and the hypotube, and the second material is placed over the mandrel and under the first material. The first material has an outer diameter than is greater than the outer diameter of the second material. A shrink tube of heat-shrink material is then placed around at least a junction of the first and second materials. The shrink tube is heated, the first and second materials cooled, and the shrink tube and hypotube removed. In some embodiments, the shrink tube, first material, and second material are centered between two heating dies configured to form a circle around the shrink tube, first material, and second material. In one embodiment, the shrink tube, first material, and second material are heated to a temperature of about 250° F. to 500° F. The heating time may be between about 0.25 to 60 seconds. The methods reduce the possibility of human error and increase consistency of the distal tips produced.

In other embodiments, the methods include placing a first polyether block amide having a first Shore D durometer hardness over the mandrel and the hypotube, and placing a second polyether block amide having a second Shore D hardness that is greater than the first Shore D hardness over the mandrel and under the first polyether block amide. The first polyether block amide generally has a Shore D hardness of about 50 D to 60 D, while the second polyether block amide typically has a Shore D hardness of about 60 D to 70 D. In an exemplary embodiment, the first polyether block amide has Shore D hardness of about 55 D, and the second polyether block amide has a Shore D hardness of about 63 D.

In alternative embodiments, the methods include providing a holding hypotube with a distal leg and a distal back. The tip first material is placed over the mandrel and the distal leg, and the tip second material is placed over the mandrel and under the first material so that the second material abuts the distal leg. The first material has an outer diameter than is greater than the outer diameter of the second material. In one embodiment, the first material abuts the distal back of the hypotube. In a further aspect, a catheter is formed including a distal tip formed according to the methods described herein.

Both the foregoing general description and the following detailed description are exemplary and explanatory in nature and are intended to provide an understanding of the present disclosure without limiting the scope of the present disclosure. In that regard, additional aspects, features, and advantages of the present disclosure will become apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
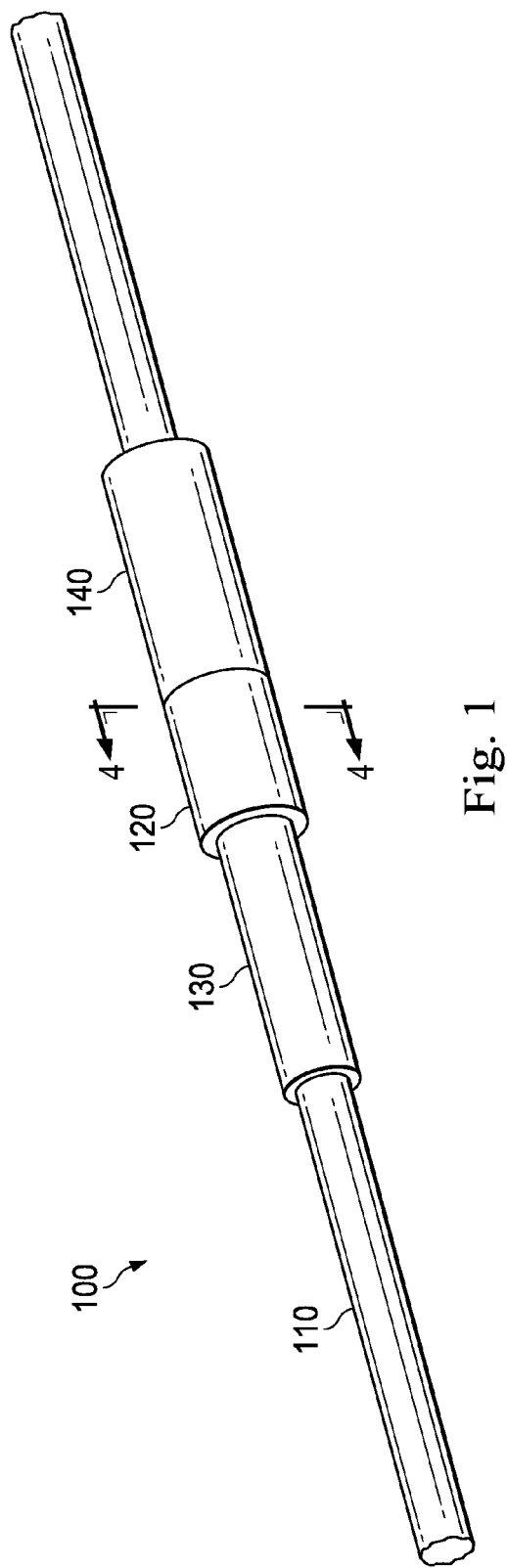
FIG. 1 illustrates a subassembly of two tip materials to be bonded according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring to FIG. 1, a subassembly 100 for forming a tapering distal tip for a catheter is shown. The tip first material 120, tip second material 130 and holding hypotube 140 are assembled over the mandrel 110. The mandrel 110 may be a metal tube or other suitable material thin enough to pass through the inner lumens of tip first material 120, tip second material 130, and holding hypotube 140. The mandrel 110 is positioned in the inner lumens of the tip first material 120 and tip second material 130 to keep the inner lumens open during the fusing of the tip first and second materials 120, 130. In one embodiment, the mandrel 110 has a diameter of about 0.010 inches to about 0.100 inches. In an exemplary embodiment, the mandrel 110 has a diameter of about 0.042 inches.

The tip first material 120 and tip second material 130 are any materials suitable for forming a flexible distal tip. In an exemplary embodiment, the tip first and second materials 120, 130 include a polyether block amide, such as Pebax® thermoplastic polymers available from Arkema Inc. The flexible materials are inexpensive and create a strong bonding surface that aids in tensile strength. The flexible materials also allow the original shape to be retained after going around tortuous paths. Advantageously, the materials can be used on the distal section of a catheter to guide the unit during an operation.

Figure 2A:
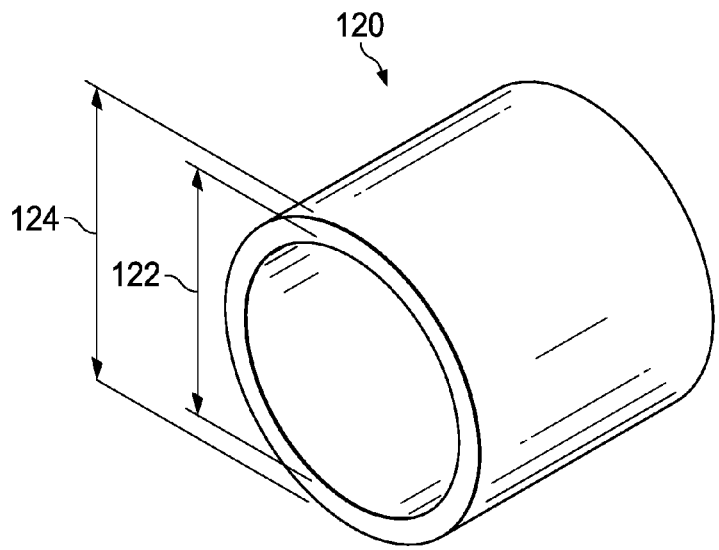
FIGS. 2A and 2B are perspective views of the tip first and second materials, respectively, prior to being bonded.

Moving now to FIG. 2A, the tip first material 120 has an inner diameter 122 and an outer diameter 124. The inner diameter 122 may measure about 0.010 inches to 0.500 inches, and the outer diameter 124 may measure about 0.050 inches to about 0.750 inches. In one embodiment, the inner diameter 122 measures about 0.062 inches and the outer diameter 124 measures about 0.100 inches. In another embodiment, the tip first material 120 includes a polyether block amide having a Shore D durometer hardness of about 25 D to about 72 D, and in an exemplary embodiment, about 50 D to about 60 D. For example, the tip first material 120 may include Pebax® 55 D.

Figure 2B:
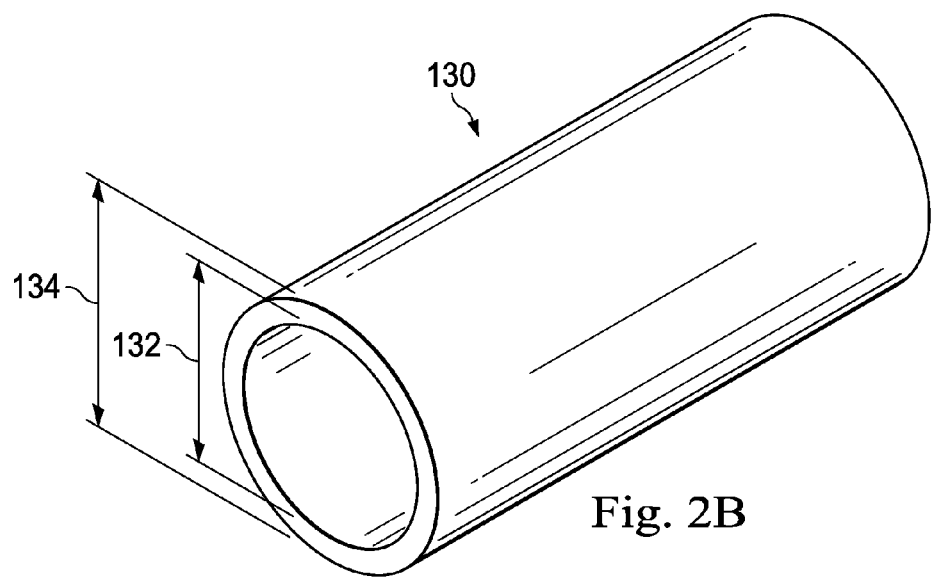

Turning to FIG. 2B, the tip second material 130 has an inner diameter 132 and an outer diameter 134. The inner diameter 132 may measure about 0.010 inches to about 0.100 inches, and the outer diameter 134 may measure about 0.025 inches to about 0.250 inches. In one embodiment, the inner diameter 132 measures about 0.051 inches and outer diameter 134 measures about 0.061 inches. In another embodiment, the tip second material 130 includes a polyether block amide having a Shore D durometer hardness of about 25 D to about 72 D, and in an exemplary embodiment 60 D to 70 D. For example, the tip second material 130 may include Pebax® 63 D.

The outer diameter 124 of the tip first material 120 is greater than the outer diameter 134 of the tip second material 130. This facilitates the method of the present disclosure by allowing tip second material 130 to slide under or within the tip first material 120.

Figure 3:
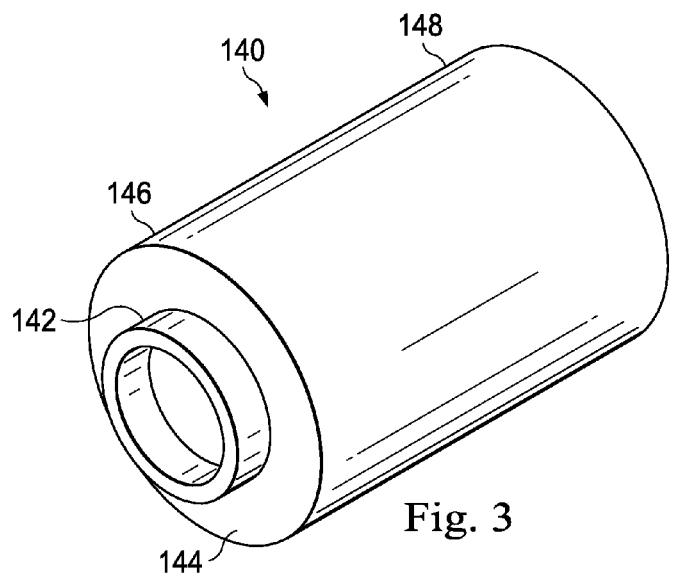
FIG. 3 is a perspective view of a holding hypotube.

FIG. 3 illustrates a holding hypotube 140. The holding hypotube 140 includes a proximal portion 148 and a distal portion 146. The holding hypotube 140 is a metal alloy tubing that provides support during the manufacturing method. The distal portion 146 includes a distal leg 142 and a distal back 144. The distal leg 142 protrudes from the distal back 144 in one direction and extends into an inner lumen of the proximal portion 148 in another direction. The outer diameter of the distal leg 142 may measure about 0.010 inches to about 0.250 inches, and the inner diameter of the distal leg 142 may measure about 0.010 inches to about 0.100 inches. In an exemplary embodiment, the distal leg 142 is a cylindrical projection with an outer diameter of about 0.059 inches and an inner diameter of about 0.050 inches. In one embodiment, the distal leg 142 extends about 0.010 inches to about 0.100 inches from the distal back 144. In an exemplary embodiment, the distal leg 142 extends about 0.044 inches from the distal back 144. In an alternative embodiment, the distal back 144 is a shoulder extending between an outer diameter of about 0.050 inches to about 0.100 inches for proximal portion 148 and about 0.010 inches to about 0.250 inches for the outer diameter of the cylindrical projection. In an exemplary embodiment, the shoulder extends between an outer diameter of about 0.100 inches for proximal portion 148 and 0.059 inches for the outer diameter of the cylindrical projection.

Figure 4:
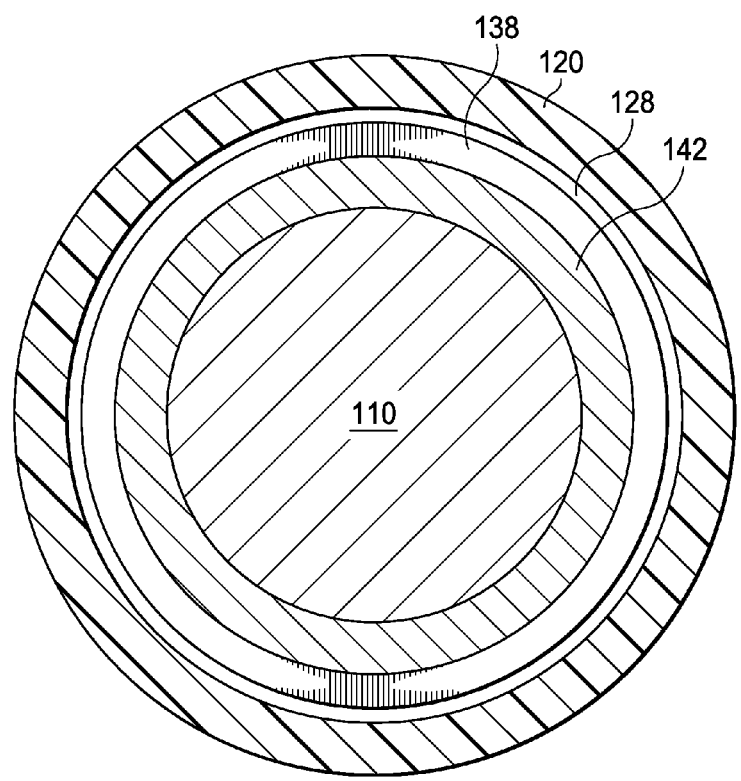
FIG. 4 is a diagrammatic cross-section of the subassembly of FIG. 1 taken along line 4-4.

FIG. 4 illustrates the cross-section of the subassembly 100 of FIG. 1 taken along line 4-4. As can be seen, the tip first material 120 is placed over the distal leg 142, and the distal leg 142 is placed over the mandrel 110. The dimensions of the tip first material 120, tip second material 130, the distal leg 142, the distal back 144, and the mandrel 110 are chosen so that this arrangement occurs. The proximal end 138 of the tip second material 120 is shown as its outer diameter is larger than the outer diameter of the cylindrical projection. Between the first tip material 120 and the tip second material 130 is an air gap 128. In an exemplary embodiment, the air gap 128 separates the second tip material 130 and the tip first material 120 by about 0.0001 inches to about 0.0100 inches. In an exemplary embodiment, the tip first material 120 and tip second material 130 are separated by about 0.001 inches. The air gap 128 eases assembly of the components and is eliminated as the parts melt during the manufacturing process.

The method of forming a tapering distal tip will now be described. The method begins by providing the mandrel 110 and holding hypotube 140. The tip first material 120 and the tip second material 130 are cut and placed distally over the mandrel 110 and the holding hypotube 140.

Figure 5:
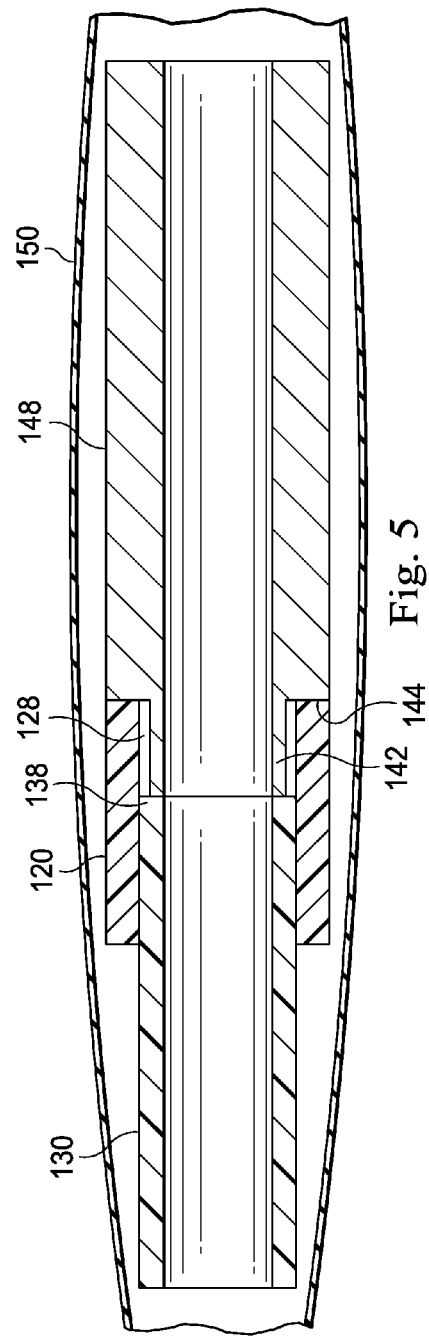
FIG. 5 is a diagrammatic cross-sectional side view of the subassembly of FIG. 1.

Specifically, referring to FIG. 5, the tip first material 120 is placed over the mandrel and the distal leg 142 of the holding hypotube 140. The tip first material 120 butts up to the distal back 144. The tip first material 120 merely touches the edge of the distal back 144, but does not go over the proximal portion 148 of the holding hypotube 140. The air gap 128 includes the space between the distal leg 142 and the tip first material 120. The tip second material 130 is placed over the mandrel and within the inner lumen of the tip second material 130. The tip second material 130 butts up to the distal leg 142 of the hypotube 140. Since the outer diameter of the distal leg 142 is greater than the inner diameter of the tip second material 130, the proximal end 138 of the tip second material 130 merely touches the edge of the distal leg 142, but does not go over it. The mandrel 110 is removed from FIG. 5 for ease of illustration.

Next, a shrink tube 150 of heat-shrink material is placed over the junction between the tip first material 120 and the tip second material 130, as well as over the holding hypotube 140. Bonding of the tip first and second materials 120, 130 is completed by applying heat to the shrink tube 150 to melt the first and second materials 120, 130, while also shrinking the shrink tube 150.

The shrink tube 150 may be manufactured from a material that will prevent a permanent adhesion of the shrink tube 150 to the first and second tip materials 120, 130, so that shrink tube 150 can be easily removed (for example, by peeling off)

at the end of the bonding process. Similarly, mandrel 110 may be manufactured from or coated with a material that will not adhere to the inner lumen of the first and second tip materials 120, 130.

In one embodiment, heating shrink tube 150 involves centering shrink tube 150, tip first material 120, and tip second material 130 between two heating dies configured to form a circle around the shrink tube 150, tip first material 120, and tip second material 130. The top of the dies may be used to pre-shrink the shrink tube 150. The shrink tube 150, tip first material 120, and tip second material 130 are heated to between about 250° F. to 500° F. for about 0.25 to 60 seconds. Heat is applied by a hot box and verified with thermocouples.

In an exemplary embodiment, the time and temperature of the heating machine is automatically controlled so the operator's task is limited to pre-shrinking and placement in the dies. Since the placement in the machine may be controlled by a micrometer, the operator is able to place the shrink tube 150, tip first material 120, and tip second material 130 in the same location every time. Any operator can be trained on these steps, increasing the consistency of the formed tip. After placement between the dies, a button may be pushed that triggers the machine to heat for a specific time. Once the appropriate time and temperature are reached, the dies that are heating the shrink tube 150, tip first material 120, and tip second material 130 can automatically open. The operator then cools the part and removes the shrink tube 150.

During heating, the shrink tube 150 shrinks and constrains a flow of first and second materials 120, 130. As first and second materials 120, 130 melt, they fuse together to form a composite tip having different thicknesses and material properties. The distal most portion of the tip is formed entirely of tip second material 130, making it the most flexible area. The proximal portion of the tip is formed entirely of tip first material 120, making it more rigid than the distal portion of tip first material 120. The tapering transition zone 125 is formed of both materials and allows a smooth transition in stiffness between the distal and proximal portions. After cooling first and second materials 120, 130, shrink tube 150 and holding hypotube 140 are removed to yield a flexible distal tip. The inner diameter of the distal tip has been molded during the heating process to match the mandrel 110 outer diameter over most of the length with an enlarged inner diameter matching the outer diameter of the distal leg 142 at the proximal portion.

Figure 6:
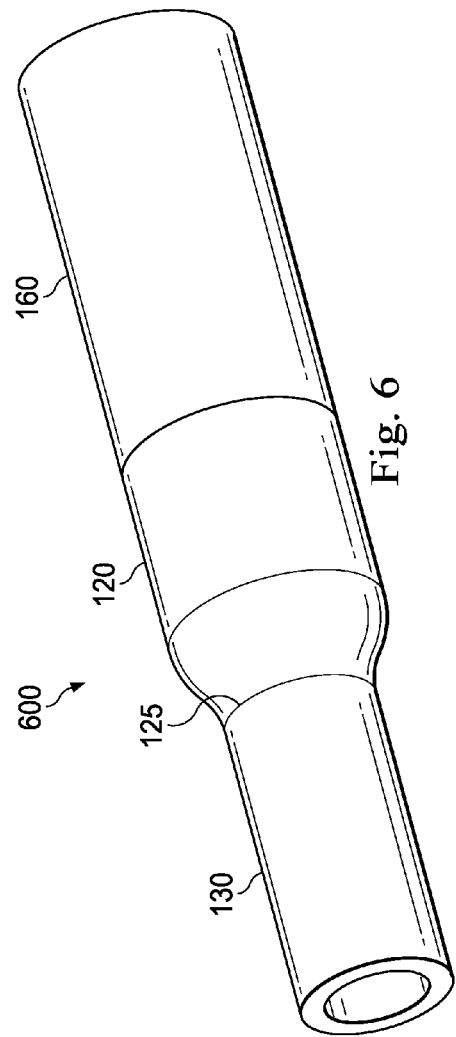
FIG. 6 illustrates a tapered distal tip formed according to various aspects of the present disclosure.

Referring to FIG. 6, distal tip 600 includes tip first material 120 and tip second material 130. As illustrated, distal tip 600 is bonded to an imaging hypotube 160. Shrink tube 150 created a smooth and long transition zone from the tip first material 120 to the tip second material 130 over their junction. The resulting bond is strong and flexible, with a transition zone of blended material properties, rather than an abrupt transition. The length of the distal tip may be about 5 mm to 15 mm. In an exemplary embodiment, the length of the distal tip 600 is about 12 mm.

The methods described herein are simpler, less expensive, save time, reduce the possibility of human error and improve reproducibility by introducing automated machines. Automated heating devices help control the consistency of the tip, which lowers the scrap ratio. There is no added step for a mis-shaped part, reducing the assembly time. This process can be duplicated by any operator, giving a more lean manufacturing line and improving the consistency.

The tip can be made as a sub-assembly, which increases stock and ultimately saves time and money. Also, time and money decrease because the two materials can be ordered in bulk and pre-trimmed.

Persons skilled in the art will recognize that the devices and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of forming a tapering distal tip for a catheter, comprising:
   providing a mandrel and a holding hypotube;
   placing a tip first material with a first outer diameter over the mandrel and the hypotube;
   placing a tip second material with a second outer diameter over the mandrel and under the first material, the first outer diameter being greater than the second outer diameter;
   placing a shrink tube of heat-shrink material around at least a junction of the first material and second material;
   heating the shrink tube;
   cooling the first material and second material; and
   removing the shrink tube and the hypotube.

2. The method of claim 1, wherein the first material comprises a polyether block amide having a Shore D durometer hardness of about 50 D to 60 D and the second material comprises a polyether block amide having a Shore D durometer hardness of about 60 D to 70 D.

3. The method of claim 1, wherein the first material has a Shore D durometer hardness of about 55 D and the second material has a Shore D durometer hardness of about 63 D.

4. The method of claim 1, wherein the first material abuts a distal back of the hypotube.

5. The method of claim 1, wherein the second material abuts a distal leg of the hypotube.

6. The method of claim 1, wherein heating the shrink tube comprises centering the shrink tube, first material, and second material between two heating dies configured to form a circle around the shrink tube, first material, and second material.

7. The method of claim 6, wherein the shrink tube, first material, and second material are heated between about 250° F. to 500° F.

8. The method of claim 7, wherein the shrink tube, first material, and second material are heated for about 0.25 to 60 seconds.

9. A method of forming a tapering distal tip for a catheter, comprising:
   providing a mandrel and a holding hypotube;
   placing a first polyether block amide having a first Shore D durometer hardness over the mandrel and the hypotube;
   placing a second polyether block amide having a second Shore D durometer hardness that is greater than the first Shore D durometer hardness over the mandrel and under the first polyether block amide;
   placing a shrink tube of heat-shrink material around at least a junction of the first polyether block amide and the second polyether block amide;
   centering the shrink tube, first material, and second material between two heating dies configured to form a circle around the shrink tube, first material, and second material;

cooling the first polyether block amide and the second polyether block amide; and removing the shrink tube and hypotube.

10. The method of claim 9, wherein the first polyether block amide abuts a distal back of the hypotube.

11. The method of claim 9, wherein the second polyether block amide abuts a distal leg of the hypotube.

12. The method of claim 9, wherein the shrink tube, first polyether block amide, and second polyether block amide are heated between about 250° F. to 500° F.

13. The method of claim 12, wherein the shrink tube, first polyether block amide, and second polyether block amide are heated for about 0.25 to 60 seconds.

14. A method of forming a tapering distal tip for a catheter, comprising:
   providing a mandrel and a holding hypotube, the hypotube comprising a distal leg and a distal back;
   placing a tip first material with a first outer diameter over the mandrel and the distal leg;
   placing a tip second material with a second outer diameter over the mandrel and under the first material so that the second material abuts the distal leg, the first outer diameter being greater than the second outer diameter;
   placing a shrink tube of heat-shrink material around at least a junction of the first material and second material;
   heating the shrink tube;
   cooling the first material and second material; and
   removing the shrink tube and the hypotube.

15. The method of claim 14, wherein the first material comprises a polyether block amide having a Shore D durometer hardness of about 55 D and the second material comprises a polyether block amide having a Shore D durometer hardness of about 63 D.

16. The method of claim 14, wherein the first material abuts the distal back of the hypotube.

17. The method of claim 14, wherein heating the shrink tube comprises centering the shrink tube, first material, and second material between two heating dies configured to form a circle around the shrink tube, first material, and second material.

18. The method of claim 14, wherein the shrink tube, first material, and second material are heated between about 250° F. to 500° F.

19. The method of claim 18, wherein the shrink tube, first material, and second material are heated for about 0.25 to 60 seconds.

* * * * *